United States Patent
Matsumoto et al.

(10) Patent No.: US 6,667,419 B1
(45) Date of Patent: Dec. 23, 2003

(54) METHOD FOR ABSORPTION OF ACRYLIC COMPOUND AND APPARATUS THEREFOR

(75) Inventors: Yukihiro Matsumoto, Kobe (JP); Takeshi Nishimura, Himeji (JP); Misao Inada, Himeji (JP); Kazuhiko Sakamoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/605,219

(22) Filed: Jun. 28, 2000

(30) Foreign Application Priority Data

Jul. 6, 1999 (JP) .......................... 11-191816

(51) Int. Cl.⁷ .................. C07C 51/42; C07C 51/16
(52) U.S. Cl. .............. 562/600; 562/485; 562/532; 562/538; 562/545
(58) Field of Search .................. 562/600, 485, 562/532, 538, 545

(56) References Cited

U.S. PATENT DOCUMENTS

| | | |
|---|---|---|
| 3,868,417 A | 2/1975 | Duembgen et al. ..... 260/526 N |
| 3,957,880 A | 5/1976 | Sate et al. ............ 260/604 HF |
| 4,092,132 A | 5/1978 | Leacock ..................... 55/48 |
| 4,333,894 A | 6/1982 | Hoppe et al. ................. 261/96 |
| 4,543,219 A | 9/1985 | Yamato et al. .............. 261/109 |
| 5,426,221 A | * 6/1995 | Willersinn ................... 562/600 |
| 5,780,679 A | * 7/1998 | Egly et al. ................... 562/600 |
| 5,785,821 A | 7/1998 | Sakamoto et al. |

FOREIGN PATENT DOCUMENTS

EP 0856343 A1 8/1998 ............ B01D/3/16

* cited by examiner

Primary Examiner—Alan L. Rotman
Assistant Examiner—Taylor V. Oh
(74) Attorney, Agent, or Firm—Mathews, Collins, Shepherd & McKay, P.A.

(57) ABSTRACT

A method for the absorption of (meth)acrylic acid and/or (meth)acrolein and an apparatus thereof which, in an absorption column adapted to cause an (meth)acrylic acid and/or (meth)acrolein-containing gas obtained in consequence of catalytic gas phase oxidation to come into countercurrent contact with a solvent, contemplate using a packing of relatively high efficiency in absorption disposed on the upstream side of the flow of a liquid containing the solvent and a packing and/or trays of relatively low performance of forming polymerization disposed on the downstream side thereof, in the column.

11 Claims, 2 Drawing Sheets

METHOD FOR ABSORPTION OF ACRYLIC COMPOUND AND APPARATUS THEREFOR

BACKGROUND OF THE INVENTION

1. Field of the Invention

This invention relates to a method for absorbing (meth)acrylic acid and/or (meth)acrolein and an apparatus therefor More specifically, it relates to a method for absorbing (meth)acrylic acid and/or (meth)acrolein in the operation of an absorption column so adapted as to collect a (meth)acrylic acid and/or (meth)acrolein -containing gas, for example, arising from catalytic gas phase oxidation by causing the gas to contact a solvent for the purpose of effecting efficient absorption of the gas while preventing the (meth)acrylic acid or the like from polymerization and an apparatus therefor.

2. Description of the Related Art

From the gas containing (meth)acrylic acid which is obtained by subjecting propylene, for example, to catalytic gas phase oxidation with a molecular oxygen-containing gas in the presence of an oxidizing catalyst, the solution of (meth)acrylic acid, for example, is obtained by leading the gas to an absorption column for (meth)acrylic acid and allowing the gas to cool therein by contact with a solvent.

Generally by technological reasons, the absorption column is of the packing type. U.S. Pat. No. 5,785,821 proposes use of a random packing (cascade mini rings) and U.S. Pat. No. 5,780,679 proposes use of a sheet structured packing (MELLAPAK) in the absorption column of this type. The column, however, requires an unduly large height for the purpose of effecting the absorption of (meth)acrylic acid, for example, with as high efficiency as expected. Since the absorption column entails gradual adhesion of a polymer to the interior thereof and encounters gradual decline of the efficiency of absorption with the elapse of the time spent for its operation, it rather frequently calls for a work of interrupting the operation of the column and removing the adhering polymer.

SUMMARY OF THE INVENTION

It is an object of this invention, therefore, to solve such problems of the prior art as mentioned above and provide a method for absorbing (meth)acrylic acid and/or (meth)acrolein in the absorption column for (meth)acrylic acid and/or (meth)acrolein for the purpose of effecting the required absorption of the compound with high efficiency while preventing the compound from succumbing to polymerization and an apparatus therefor.

The object of this invention is accomplished by providing, in an absorption column adapted to establish countercurrent contact between the gas containing (meth)acrylic acid and/or (meth)acrolein arising from catalytic gas phase oxidation and a solvent, a method for absorbing (meth)acrylic acid and/or (meth)acrolein, which is characterized by having a packing of relatively high efficiency of absorption installed on the upstream side of the flow of a liquid containing the solvent and a packing and/or a plate tower of relatively low performance of polymerization installed on the downstream side thereof, inside the column.

The object of this invention is further accomplished by providing, in an absorption column adapted to establish countercurrent contact between the gas containing (meth)acrylic acid and/or (meth)acrolein arising from catalytic gas phase oxidation and a solvent, an apparatus for the absorption of (meth)acrylic acid and/or (meth) acrolein, which is characterized by having a packing of relatively high efficiency of absorption installed on the upstream side of the flow of a liquid containing the solvent and a packing and/or a plate tower of relatively low performance of polymerization installed on the downstream side thereof, inside the column.

The method of this invention is capable of absorbing (meth)acrylic acid and/or (meth)acrolein with high efficiency and satisfactorily preventing (meth)acrylic acid and/or (meth)acrolein from polymerization as well owing to the use of a packing and/or tray of different kinds.

The apparatus of this invention is enabled by a simple configuration to effect absorption of (meth)acrylic acid and/or (meth)acrolein with high efficiency and, at the same time, preclude (meth)acrylic acid and/or (meth)acrolein from polymerization.

DESCRIPTION OF THE PREFERRED EMBODIMENTS

Figure 1:
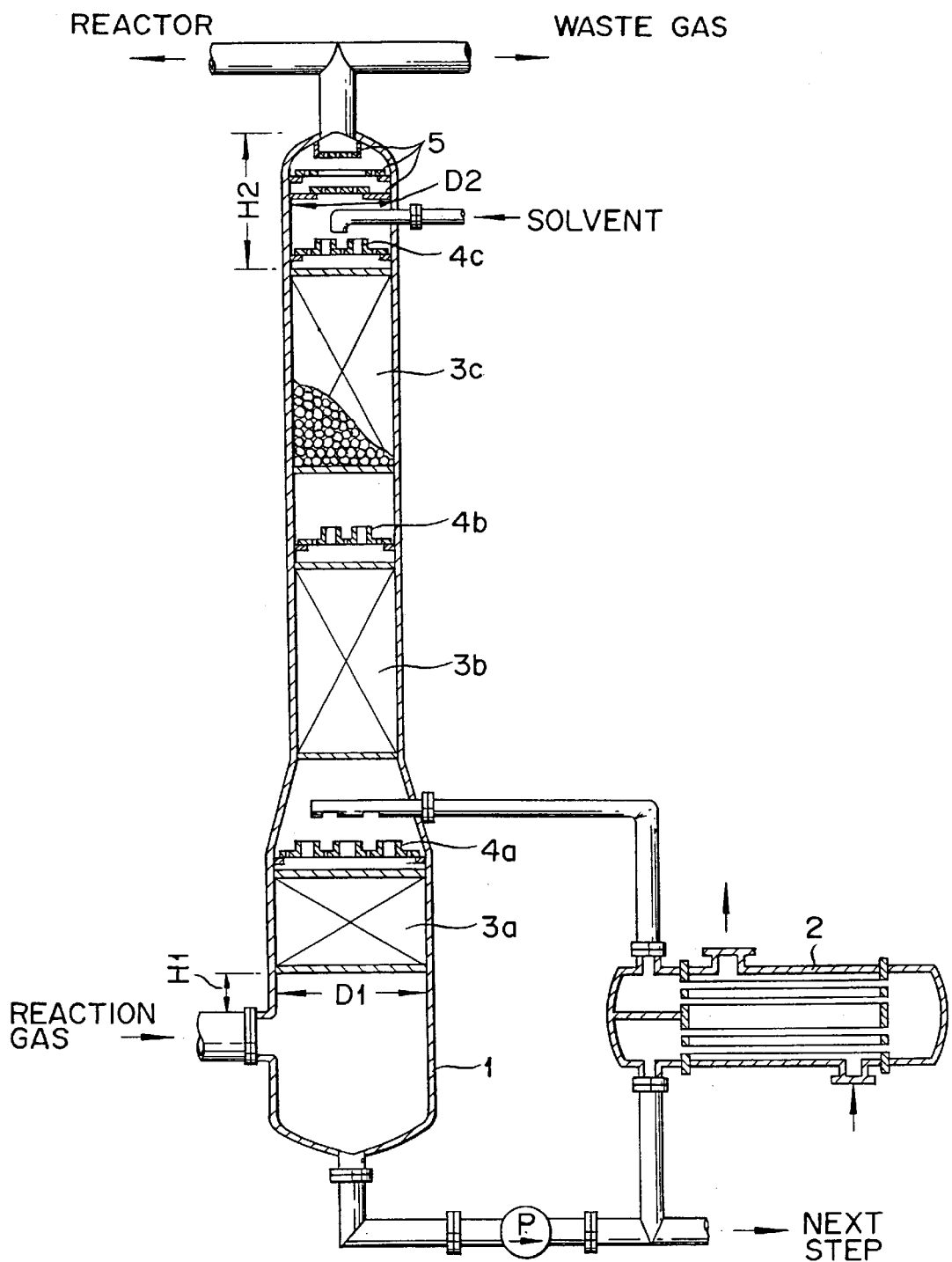
FIG. 1 is an explanatory diagram of the interior of an absorption column provided with a cooler in one embodiment of this invention.

Now, this invention will be described in detail below with reference to a (meth)acrylic acid-containing gas as a typical example.

The (meth)acrylic acid-containing gas (referred to otherwise as "reaction gas") which is obtained, for example, by subjecting propylene to catalytic gas phase oxidation with a molecular oxygen-containing gas in the presence of an oxidizing catalyst (reference to Encyclopedia of Chemical Processing and Design. MARCEL DEKKER, INC., Vol. 1, 1976, pp 409 to 413 relative to acrylic acid and to Hydrocarbon Processing, November 1983, pp 116 relative to methacrylic acid recommended) is discharged from a reactor generally at a temperature in the range of 200 to 350° C., passed through a waste heat boiler, a cooler, and so on, and supplied at a temperature in the range of 100 to 300° C. to an absorption column for (meth)acrylic acid.

A (meth)acrylic acid-containing gas is generally introduced through the lower part of an absorption column, on the other hand a solvent for absorbing the (meth)acrylic acid is introduced through the upper part thereof to establish countercurrent contact with the gas in the absorption column. The absorption column or tower to be used herein may be any of known absorption columns such as a plate tower, a packed tower, a wetted-wall tower, and a spray tower. The absorption column of this nature is generally preferred to be a plate tower or a packed tower. This column is charged in the interior thereof with packings or trays. In the case of packed column, a packing having a large surface area and manifesting high gas-permeability is regularly or irregularly filled in the interior thereof. The column carries out the gas-liquid contact on the surface of packings.

The solvent to be fed to the absorption column may be any of known solvents such as water, a water containing an organic acid ((meth)acrylic acid subjected to the absorption, acetic acid and the like), and inert hydrophobic organic liquids of high boiling points (biphenyl ether, biphenyl, or the like). These solvents may be used either singly or in combination of two or more members. Such a solvent is preferred, for the purpose of preventing a polymerizable substance such as (meth)acrylic acid from polymerization, to incorporate suitably therein any of polymerization inhibitors such as methoquinone, manganese acetate, nitrosophenol, cupherron, N-oxyl compounds, copper dibutylthiocarbamate, phenothiazine, and hydroquinone.

In this invention, a packing manifesting relatively high efficiency in the absorption of (meth)acrylic acid and/or (meth)acrolein is installed on the upstream side of the flow of the solvent mentioned above or a liquid containing the solvent and a packing and/or trays having relatively low performance of forming polymer of (meth)acrylic acid and/or (meth)acrolein on the downstream side of the flow, in the column. The term "relatively high (low)" used herein means that, when a plurality of packings are separately used, the packing under discussion exhibits the relevant quality at a higher level than the other packings. The expression "a packing having relatively low performance of forming polymer," for example, means that when the absorption column is loaded with a plurality of packings respectively, it refers to the packing that has a lower performance of forming polymer than the rest of packings. Generally, since the solvent and the (meth)acrylic acid-containing gas are brought into countercurrent contact in the column, the upstream side is properly located in the upper part of the absorption column and the downstream side in the lower part of the absorption column, namely in the direction toward the entrance for the (meth)acrylic acid-containing gas.

The substances which fill the interior of the absorption column are packings and trays, for example. In the general absorption column, gauze structured packings manifest the highest efficiency in the absorption, followed sequentially by sheet structured packings, random packings, grid structured packings, and trays. Among other trays of varying kinds, those of high performance equal the sheet structured packings and the random packings in terms of this performance. In terms of the ease with which the (meth)acrylic acid, for example, is allowed to polymerize, the gauze structured packings occupy the highest rank, sequentially followed by the sheet structured packings, random packings, the grid structured packings, and the trays.

When the gauze structured packing, for example, is used to heighten the efficiency of absorption, since this packing tends to polymerize a substance under treatment, the use of this packing entails a problem of polymerization and disables the absorption column from permitting a protracted operation. When the grid structured packing, for example, is used to prevent the substance under treatment from polymerization, since this material is deficient in the efficiency of absorption, the use of the packing requires the column to have an unduly large height to acquire the prescribed efficiency. By using the gauze structured packing on the upstream side in the flow of the liquid containing a solvent and using at least one member selected from the group consisting of the sheet structured packing, the random packing, the grid structured packing, and the trays, in particular preferably the sheet structured packing and/or the random packing on the downstream side thereof, in the column, therefore, the prevention of polymerization and the exaltation of the efficiency of absorption are simultaneously fulfilled and the protracted stable operation of the absorption column is realized.

The gauze structured packings include SULZER Packing (available from Sumitomo Heavy Industries Co., Ltd. in Japan), Technopack (available from Mitsui & Co., Ltd. in Japan), and M. C. Packing (available from Mitsubishi Chemical Engineering Co., Ltd. in Japan) and the like; the sheet structured packings include MELLAPAK (available from Sumitomo Heavy Industries Co., Ltd. in Japan), Technopack (available from Mitsui & Co., Ltd. in Japan), and M. C. Pack (available from Mitsubishi Chemical Engineering Co., Ltd. in Japan); the grid structured packings include Flexigrid (available from KOCH ENGINEERING CO. INC.) and the like; the random packings include raschig rings, pall ring, cascade mini rings (available from Dodwell Corp), and IMTP (available from Norton Corp) and the like; and the trays include sieve trays, valve trays, dualflow trays, bubble cap trays, baffle trays, SUPERRRAC Trays, ripple trays, and jet trays.

Among other random packings, the cascade mini rings and IMTP which have flat shapes prove particularly advantageous because they are capable of nearly structured packing, excellent in the prevention of polymerization, and high efficiency of absorption.

The bed made of the packings may be formed so as to fill up the whole interior of the absorption column or may be formed as split into a plurality of steps so as to prevent the gas and liquid from forming a channeling. The packings may be filled through manholes in the column according to the conventional manner.

The operating conditions in the absorption column are decided by factors such as pressure, temperature, composition of the liquid for absorption, and amount of the liquid for absorption. Though the temperature is preferred to be low and the amount of the liquid for absorption to be large, they are restricted by the subsequent step of operation. The appropriate conditions, therefore, are set with these factors taken into consideration.

The term "absorption column" generally refers to a column which is provided in the interior thereof with a region for allowing the (meth)acrylic acid-containing gas to come into countercurrent contact with the solvent. This term, therefore, embraces the case of effecting the absorption by the use of one column and the case of effecting the absorption by the use of a plurality of columns as well. From the viewpoint of economy, the absorption by an absorption column is commendable.

Since it has been ascertained that the ease with which the (meth)acrylic acid in the liquid phase of the interior of the absorption column is polymerized is varied by the concentration of the (meth)acrylic acid, it is commendable to select the kind of the packing based on the concentration of the (meth)acrylic acid. To be specific, the (meth)acrylic acid concentration in the liquid phase of the interior of the column in the steady state of absorption is generally in the range of 3 to 60% by weight, preferably 4 to 40% by weight, and more preferably 5 to 30% by weight. Preferably, the part having a liquid concentration smaller than the lower limit of the range mentioned above is assigned as the upstream side of the flow of the liquid containing the solvent and the part having a liquid concentration larger than the upper limit of the range as the downstream side of the flow, inside the column. By installing generally a plurality of beds or trays having the packing placed as split in the manner described above, it is possible to effect efficient absorption of the (meth)acrylic acid in the solvent and meanwhile preclude the (meth)acrylic acid from polymerization. Where the (meth)acrylic acid concentration is in the range of 3 to 60% by weight, it is permissible to assign the upstream side and the downstream side with an arbitrary concentration in this range such as 10% by weight as the boundary.

After the catalytic gas phase oxidation, it is preferable to introduce the produced (meth)acrylic acid-containing gas into the absorption column through the lower part thereof, forward part of the (meth)acrylic acid solution withdrawn through the bottom part of the column to the subsequent refining step, allow the remainder of the solution to cool in an external cooler, and introduce the resultant condensate into the absorption column and allow it to contact the gas in counter flow and cool till condensation. In this case, generally the resultant cooling liquid is preferred to be circulated in such a manner that the liquid-gas ratio may fall in the range of 2 to 15 L (liter)/$Nm^3$, preferably 3 to 12 L/$Nm^3$, and more preferably 5 to 10 L/$Nm^3$. By setting the ratio in this range, it is possible to heighten the efficiency of absorption of the (meth)acrylic acid. The cooler to be used herein is not particularly restricted but only required to be a heat exchanger which is capable of indirectly cooling the liquid. Suitable heat exchangers may include a shell-and-tube heat exchanger, a double-pipe heat exchanger, a spiral type heat exchanger, and a plate type heat exchanger. As respects the extent of cooling, the absorption column is cooled so that the temperature at a certain point in the interior of the column may reach a predetermined level. Generally, the cooling is controlled by the tower top temperature. Further, the position of the absorption column at which the cooling liquid obtained at the cooler is circulated to the absorption column is generally in the range of 1 to 10 theoretical plate number, preferably 1 to 5 theoretical plate number, and further preferably 2 to 4 theoretical plate number, from the position for the withdrawal of the liquid.

The (meth)acrylic acid-containing gas obtained by the catalytic gas phase oxidation is preferred to be introduced into the absorption column at a position represented by the formula, $H1=(0.5-5)\times D1$ {wherein H1 denotes the distance from the upper part of the gas inlet nozzle to the tray at the lowest level or the member for supporting the packing and D1 the diameter of the lower part of the column (naturally, the unit of the distance and the unit of the diameter equal)}. By adopting this method, it is possible to prevent the drop of efficiency of absorption due to the channeling of gas, the formation of bubbles due to the insufficient cooling of the gas, and the polymerization or flooding in the bed of packing or in the trays when the value of H1 is small. Further, the adhesion of polymer to the wall of the column can be eliminated when the value of H1 is large.

Further, the retention time of the gas in the void tower from the upper end of the gas inlet nozzle to the tray of the lowest level or the supporting member for the packing may be in the range of 1 to 5 seconds. By adopting this method, it is possible to prevent the drop of the efficiency of absorption due to the channeling of the gas, the formation of bubbles due to the insufficient cooling of the gas, and the polymerization or flooding in the bed of packing or in the trays when the retention time is small. Further, the adhesion of polymer to the wall of the column can be eliminated when the retention time is large.

The gas outlet nozzle is preferred to be opened in the absorption column at a position represented by the formula, $H2=(0.5-3)\times D2$ {wherein H2 denotes the distance from the uppermost part of the packing to the lower end of the gas outlet nozzle and D2 the diameter of the upper part of the column (naturally, the unit of the distance and the unit of the diameter equal)}. By adopting this made, it is possible to diminish the entrainment by the liquid, prevent the adhesion of deposit to the equipment and the pipes falling after the gas outlet, and lower the loss of the efficiency of absorption when the value of H2 is small. Further, the adhesion of deposit to the wall of the column can be eliminated when the value of H2 is large.

Further, the retention time of the gas in the empty space of the column from the uppermost part of the packing to the lower end of the gas outlet nozzle is preferred to be in the range of 0.5 to 3 seconds. By adopting this made, it is possible to diminish the entrainment of splash by the liquid, prevent the adhesion of deposit to the equipment and the pipes falling after the gas outlet, and lower the loss of the efficiency of absorption when the retention time is small. Further, the adhesion of deposit to the wall of the column can be eliminated when the retention time is large.

It is preferred to have a mist separator installed in the empty space of the column from the uppermost part of the packing to the lower end of the gas outlet nozzle. By adopting this method, the prevention of the entrainment of splash by the liquid can be attained more effectively. The mist separator to be used in this case may be any of the known devices of the collision plate types such as a perforated plate, a corrugated plate, and a wire mesh.

In the case of the packed columns, the dispersion of the liquid which is in the process of descending the interior of the column constitutes the most important factor regarding the efficiency of absorption. It is, therefore, preferred to have a liquid dispersing device installed not only at the liquid supply port but, when the packed column has an increased height, also at least at a point over the packing bed falling halfway along the length of the flow path in the column for the purpose of preventing the liquid from channeling. Generally, the liquid dispersing device is used in varying types such as the pipe orifice type and the gas riser liquid drip type. Since all these types are invariably designed to ensure uniform flow of the liquid through a multiplicity of holes by applying a certain amount of pressure on the holes, the holes are automatically given a small diameter and, therefore, are often clogged as with a polymer and possibly suffered to entail degradation of the efficiency of absorption and forced suspension of the operation of the column. By alternatively using the overflow type liquid dispersing device, therefore, it is possible to retain the efficiency of absorption and allow the column a protracted operation. The overflow type liquid dispersing device, for example, is of a structure which has a multiplicity of notches formed in the upper end of a liquid dispersing pipe so as to permit the liquid to be dispersed by overflowing the notches.

The method for the absorption of the (meth)acrylic acid described above is implemented by the following apparatus, i.e. the apparatus for the absorption of (meth)acrylic acid which is intended to be used in an absorption column for allowing a (meth)acrylic acid-containing gas obtained by the catalytic gas phase oxidation to make a countercurrent contact with a solvent and characterized by installing a packing of relatively high efficiency of absorption on the upstream side in the flow of a liquid containing the solvent and a packing of relatively low performance of forming a polymer and/or trays on the downstream side thereof, in the interior of the column.

In the absorption column for the (meth)acrylic acid, the apparatus for the absorption of (meth)acrylic acid is preferred to use a gauze structured packing on the upstream side of the flow of the liquid containing the solvent and at least one member selected from the group consisting of a sheet structured packing, a grid structured packing, a random packing, and trays on the downstream side thereof, in the interior of the column.

In the absorption column for the (meth)acrylic acid, the apparatus for the absorption of (meth)acrylic acid is preferred to have a mist separator further installed in the upper part of the interior of the absorption column.

In the absorption column for the (meth)acrylic acid, the apparatus for the absorption of (meth)acrylic acid is preferred further to have an overflow type liquid dispersing device disposed over the upper part of at least one bed of packing.

In the absorption column for the (meth)acrylic acid, the apparatus for the absorption of (meth)acrylic acid is preferred to have a reaction gas inlet nozzle disposed at a position satisfying the relation of the formula, H1=(0.5–5)×D1, wherein H1 denotes the distance from the upper end of the gas inlet nozzle to the tray of the lowermost level or the member for supporting the packing and D1 the diameter of the lower part of the column.

In the absorption column for the (meth)acrylic acid, the apparatus for the absorption of (meth)acrylic acid is preferred to have an outlet nozzle for the treating gas of the absorption column disposed at a position satisfying the formula, H2=(0.5–3)×D2, wherein H2 denotes the distance from the uppermost part of the packing to the lower end of the gas outlet nozzle and D2 the diameter of the upper part of the column.

Now, this invention will be described more specifically below with reference to the drawings.

FIG. 1 is an explanatory diagram of the interior of a (meth)acrylic acid absorption column provided with a cooler as one embodiment of this invention. With reference to FIG. 1, the reaction gas enters an absorption column 1 through the lower part thereof, ascends the interior of the column, succumbs repeatedly to the countercurrent gas-liquid contact and allows the (meth)acrylic acid contained therein to be absorbed in the solvent, thereafter emanates partly as a waste gas from the top of the column and meanwhile returns partly as an inert gas to the reactor for the catalytic gas phase oxidation. More often, part of the gas emanating from the top of the column is recycled to the reactor and the remainder thereof discarded as a waste gas. There are times when the gas is wholly discarded as a waste gas. The solvent is introduced into the absorption column 1 through the upper part thereof, caused to descend the interior of the column as a component for absorbing (meth)acrylic acid during the gas-liquid contact, and withdrawn through the bottom part of the column. Part of the withdrawn solvent is cooled in an external cooler 2 and then circulated to the absorption column, wherein the liquid and the gas are brought into countercurrent contact at a ratio in the range of 2 to 15 L/Nm³, while the remainder thereof is forwarded to the next step for optionally refining (meth)acrylic acid.

The absorption column 1 is provided with three beds 3a, 3b, and 3c of packings. The bed 3a is formed of a random packing, the bed 3b a random packing, and the bed 3c a gauze structured packing. In this case, the (meth)acrylic acid concentration of the liquid phase of the bed 3c is not more than 60% by weight.

The inlet nozzle for the reaction gas satisfies the relation, H1=(0.5–5)×D1, wherein Hi denotes the distance from the upper end of the gas inlet nozzle to the tray of the lowermost level or the member for supporting the packing in the absorption column 1 and D1 the diameter of the column from the upper end of the gas inlet nozzle to the tray of the lowermost level or the member supporting the packing (the diameter in the lowermost part of the column when this diameter is not constant throughout the interval mentioned), and consequently enjoys a high efficiency in the absorption of (meth)acrylic acid. The gas retention time in the empty space of column from the upper end of the gas inlet nozzle to the tray of the lowermost level or to the member for supporting the packing is in the range of 1 to 5 seconds.

The absorption column 1 is provided in the top part thereof with an outlet nozzle for the reaction gas which has effected required absorption. The gas outlet nozzle satisfies the relation, H2=(0.5–3)×D2, wherein H2 denotes the distance from the uppermost part of the packing to the lower end of the gas outlet nozzle in the absorption column 1 and D2 the diameter of the column from the uppermost part of the packing to the lower end of the gas outlet nozzle (the diameter in the uppermost part of the column when this diameter is not constant throughout the interval mentioned), and consequently enjoys a high efficiency in the absorption of (meth)acrylic acid. The gas retention time in the empty space of tower from the uppermost part of the bed 3c of the highest level is in the range of 0.5 to 3 seconds.

A mist separator 5 is equipped in the empty space of upper part of the column, namely from the gas outlet nozzle to the uppermost level of the bed 3c (the liquid dispersing device when equipped) for the prevention of entrainment of splash by the liquid.

The beds 3a, 3b, and 3c of packings in the absorption column 1 are provided over the upper parts thereof respectively, with liquid dispersing devices 4a, 4b, and 4c for the purpose of enhancing the efficiency in the dispersion of the descending liquid.

Figure 2:
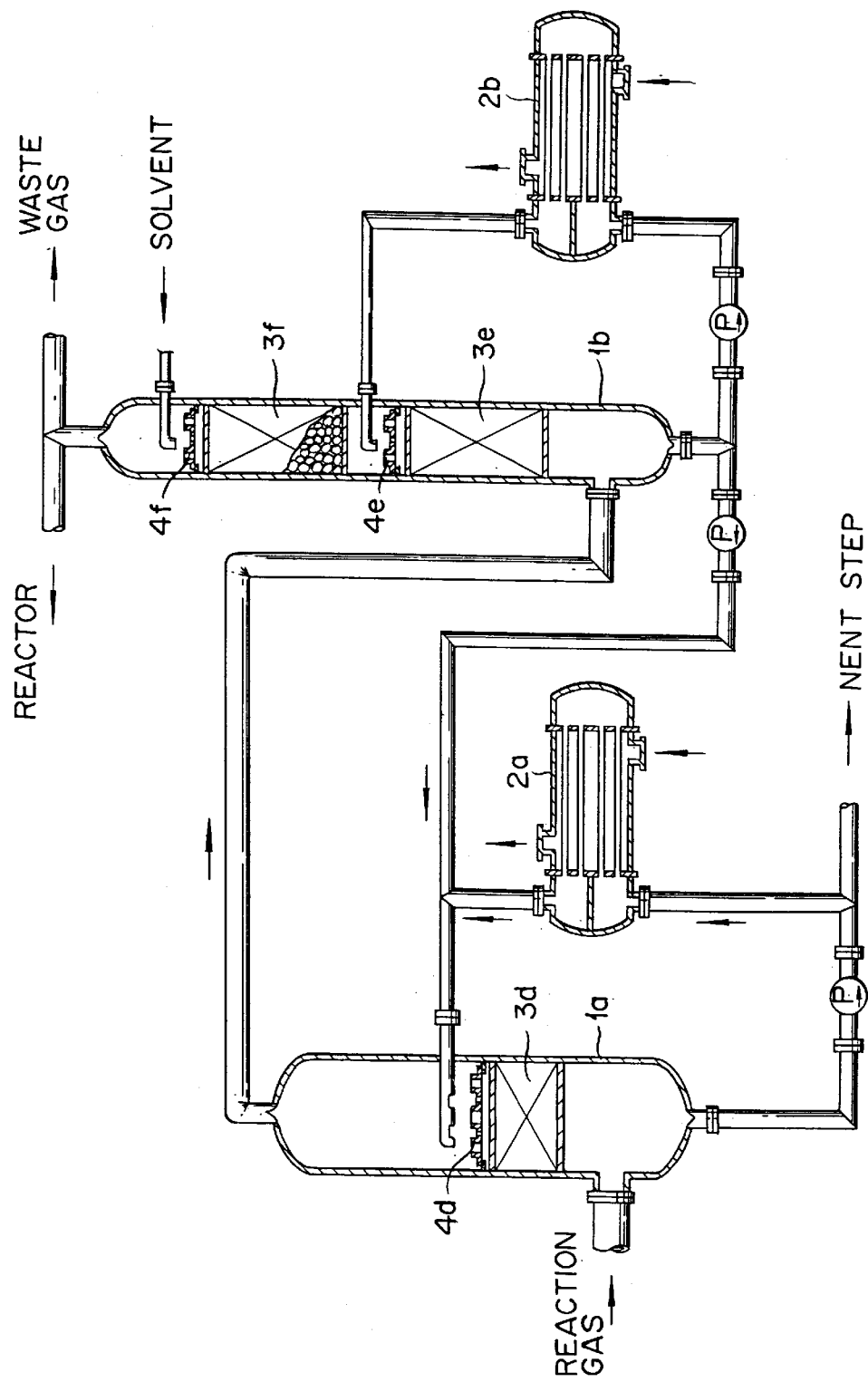
FIG. 2 is an explanatory diagram of the interior of an absorption column provided with a cooler in another embodiment of this invention.

FIG. 2 is an explanatory diagram of a (meth)acrylic acid absorption column provided with a cooler as another embodiment of this invention. FIG. 2 represents an explanatory diagram depicting provision of two absorption columns. With reference to FIG. 2, the reaction gas enters an absorption column 1a through the lower part thereof, ascends the interior of the column, succumbs repeatedly to the countercurrent gas-liquid contact and allows the (meth)acrylic acid contained therein to be absorbed in the solvent, and then repeats the countercurrent gas-liquid contact in another absorption column 1b. The gas emanating from this column 1b is either released as a waste gas from the top of the column or returned as an inert gas to the reactor for the catalytic gas phase oxidation. More often than not, part of the gas emanating from the top of the column is recycled to the reactor and the remainder thereof discarded as a waste gas. There are times when the gas is wholly discarded as a waste gas. The solvent is introduced into the absorption column 1b through the upper part thereof, and caused to descend the interior of the column as a component for absorbing (meth)acrylic acid during the gas-liquid contact. Part of the liquid withdrawn through the bottom part of the absorption column 1b is cooled in an external cooler 2b and then circulated to the absorption column 1b, wherein the liquid and the gas are brought into countercurrent contact at a ratio in the range of 2 to 15 L/Nm³, while the remainder thereof is caused to descend the interior of the absorption column 1a and brought into countercurrent contact with the reaction gas and withdrawn from the bottom part of the absorption column 1a. Part of the liquid thus withdrawn is cooled in an external cooler 2a and circulated to the absorption column, wherein the liquid and the gas are brought into countercurrent contact at a ratio in the range of 2 to 15 L/Nm³, while the remainder thereof is forwarded to the next step for optionally refining (meth)acrylic acid. It is permissible to increase the cooling capacity of the external cooler 2a and obviate the necessity for circulating the liquid to the external cooler 2b and the absorption column 1b.

The absorption column 1a is provided with a bed 3d formed of packing and the absorption column 1b is provided with beds including 3e and 3f each formed of packing, a total of three beds. In this case, two absorption columns are installed. Even when one of these columns which contains a region for effecting countercurrent gas-liquid contact between the reaction gas and the solvent and is installed separately from the other column, these two columns may well be regarded substantially as one column. The bed 3d is filled with a sieve tray, the bed 3e with a random packing, and the bed 3f with a gauze structured packing. In this case, the (meth)acrylic acid concentration in the liquid phase of the bed 3f is not more than 3 to 60% by weight.

Since a liquid dispersing device 4d is disposed over the upper part of the bed 3d in the absorption column 1a and liquid dispersing devices 4e and 4f are disposed over the upper parts respectively, of the beds 3e and 3f in the absorption column 1b, the effect in the dispersion of the descending liquid can be improved.

In the case of the system using a plurality of absorption columns, the term "upper part of an absorption column" means the upper part (the part for emitting the waste gas when the operation of absorption is completed) of the last column and the term "lower part of an absorption column" means the portion from the lower part of the first column (the part for supplying the reaction gas) through the part below the upper part of the column.

The invention has been described with reference to the case of using (meth)acrylic acid-containing gas as an inlet gas. Naturally, it can be applied to the case of using (meth)acrylic acid and/or a (meth)acrolein-containing gas as well.

EXAMPLES

Now, this invention will be more specifically described below with reference to examples.

Example 1

By the use of an absorption column 1 which comprised, as reckoned sequentially from the lower part thereof as illustrated in FIG. 1, one bed 3a measuring 400 mm in inside diameter (D1) and 2000 mm in length and using cascade mini rings 2P (available from Dodwell Corp.), two beds 3b measuring 250 mm in inside diameter (D2) and 2150 mm in length and using cascade mini rings 2P, and two beds 3c measuring 250 mm in inside diameter (D2) and 1580 mm in length and using SULZER BX (available from Sumitomo Heavy Industries Co., Ltd.), inserting a distance (H1) of 1000 mm between the upper end of the reaction gas inlet and the member supporting the packing in the lowermost part of the column and a distance (H2) of 700 mm between the packing 3c in the uppermost part of the column and the gas outlet, and incorporated in the upper empty space of column three perforated plates of 25% cut as mist separator 5 and liquid dispersing devices 4a, 4b, and 4c invariably of the overflow type (made invariably of SUS 316), absorption of acrylic acid was performed under the following operating conditions.

The absorption column was stably operated for one month with the efficiency in the absorption of acrylic acid at 99.7%. The acrylic acid concentration in the liquid phase in the lower part of SULZER BX was 6.7% by weight. After the operation, the column was opened to inspect the interior thereof. Consequently, the amount of deposit adhering to the interior of the column was found to be 0.01 kg.

Operating conditions:
a) Reaction gas: Flow volume 400 $Nm^3/h$
   Composition: 5.8 vol. % acrylic acid, 15.5 vol. % water, 73.6 vol. % nitrogen, 2 vol. % oxygen, and the balance (acetic acid, aldehyde, propylene, etc.)
b) Column top pressure: 9.8 kPaG (1000 mm $H_2O$ G), column top temperature: 62.5° C.
c) Amount of circulation in the lower part of column for passage to the cooler 2:3 $m^3/h$
d) Solvent introduced into the column through the top: Water 50 L/h (containing 100 ppm of hydroquinone as polymerization inhibitor)

The absorbed acrylic acid was recovered from the next step as illustrated in FIG. 1.

Comparative Example 1

The absorption of acrylic acid was performed by repeating the procedure of Example 1 while changing the packing invariably to SULZER BX. The acrylic acid concentration in the liquid phase in the lowermost part of the column was 65.4% by weight.

After 5 days of the operation, the loss of pressure in the column rose to the extent of disabling the operation. When the interior of the column was inspected, the amount of polymer adhering to the lower part of the column was found to be about 1 kg.

Comparative Example 2

The absorption column was operated by following the procedure of Example 1 while changing the packing 3b from cascade mini rings 2P to SULZER BX and changing the liquid dispersing devices from the overflow type to the orifice pipe type.

During the initial stage of the operation, the efficiency in the absorption of acrylic acid was 99.8% and the acrylic acid concentration in the liquid phase in the lower part of SULZER BX was 33.5% by weight. The efficiency in the absorption of acrylic acid fell to 98.7% prior to the stop of the operation. When the interior of the column was inspected, the amount of deposit adhering to the interior of the column was found to be 0.05 kg and about 40% of the orifices in the liquid distributor were clogged.

Comparative Example 3

The absorption column was operated by following the procedure of Example 1 while changing the distance (H1) from the upper end of the reaction gas inlet to the member supporting the charging material in the lowermost part of the column to 150 mm and the distance (H2) from the packing in the uppermost part of the column to the gas outlet to 100 mm, omitting the use of a mist separator in the interior of the column, and changing the amount of the liquid circulated in the lower part of the column for passage to the cooler 2 to 0.6 $m^3/h$.

After one month's operation, when the interior of the column was inspected, the amount of deposit adhering to the interior of the column was found to be 0.2 kg. The adhesion of deposit was recognized in the vapor line at the column top.

The entire disclosure of Japanese Patent Application No. 11-191816 filed on Jul. 6, 1999 including specification, claims, drawings and summary are incorporated herein by reference in its entirety.

What is claimed is:

1. A method for absorbing (meth)acrylic acid and/or (meth)acrolein, which comprises:

preparing an absorption column adapted to cause a (meth)acrylic acid and/or (meth)acrolein-containing gas to come into countercurrent contact with a solvent for absorbing the (meth)acrylic acid and/or (meth)acrolein;

disposing a packing of relatively high efficiency in absorption on the upstream side of the flow of a liquid containing the solvent and a packing and/or trays of relatively low performance of forming polymerization on the downstream side thereof, in the column, for the purpose of effecting the required absorption of the compound with high efficiency while preventing the compound from succumbing to polymerization, the upstream side and downstream side being separated with the region of the liquid phase in the absorption column having the (meth)acrylic acid and/or (meth)acrolein concentration in the range of 3 to 60% by weight as the boundary; and introducing the (meth)acrylic acid and/or (meth)acrolein-containing gas obtained in consequence of catalytic gas phase oxidation to come into countercurrent contact with the liquid separately introduced, wherein the solvent is at least one selected from the group consisting of water, acetic acid, biphenyl ether and biphenyl.

2. A method for absorbing (meth)acrylic acid and/or (meth)acrolein, which comprises:

preparing an absorption column adapted to cause a (meth)acrylic acid and/or (meth)acrolein-containing gas to come into countercurrent contact with a solvent for absorbing the (meth)acrylic acid and/or (meth)acrolein;

disposing a packing of relatively high efficiency in absorption on the upstream side of the flow of a liquid containing the solvent and a packing and/or trays of relatively low performance of forming polymerization on the downstream side thereof, in the column, for the purpose of effecting the required absorption of the compound with high efficiency while preventing the compound from succumbing to polymerization, the packing of relatively high efficiency in absorption being a gauze structured packing and the packing and/or trays of relatively low performance of forming polymerization being at least one member selected from the group consisting of a sheet structured packing, a grid structured packing, a random packing, and trays; and introducing the (meth)acrylic acid and/or (meth)acrolein-containing gas obtained in consequence of catalytic gas phase oxidation to come into countercurrent contact with the liquid separately introduced, wherein the (meth)acrylic acid and/or (meth)acrolein-containing gas is introduced into the absorption column through the lower part thereof, part of the (meth)acrylic acid and/or (meth)acrolein-containing solution withdrawn through the bottom part of the column is cooled in an external heat exchanger, and the cooling liquid is brought into countercurrent contact with the gas in such a manner that the liquid-gas ratio falls in the range of 2 to 15 L/Nm$^3$, wherein the solvent is at least one selected from the group consisting of water, acetic acid, biphenyl ether and biphenyl.

3. A method according to claim 2, wherein the upstream side and downstream side are separated with the region of the liquid phase in the absorption column having the (meth)acrylic acid and/or (meth)acrolein concentration in the range of 3 to 60% by weight as the boundary.

4. A method according to claim 3, wherein a retention time of the gas in the empty space of column from the upper end of a gas inlet nozzle to the tray of the lowermost level or the member for supporting the packing is in the range of 1–5 seconds and/or a retention time of the gas in the empty space of column from the uppermost part of a packed column to the lower end of a gas outlet nozzle is in the range of 0.5 to 3 seconds.

5. A method according to claim 4, the solvent further incorporates a polymerization inhibitor wherein the polymerization inhibitor is at least one member selected from the group consisting essentially of methoquinone, manganese acetate, nitrosophenol, cupherron, a N-oxy compound, copper dibutythiocarbamate, phenothiazine, and hydroquinone.

6. A method according to claim 1, wherein the (meth)acrylic acid and/or (meth)acrolein-containing gas is introduced into the absorption column through the lower part thereof, part of the (meth)acrylic acid and/or (meth)acrolein-containing solution withdrawn through the bottom part of the column is cooled in an external heat exchanger, and the cooling liquid is brought into countercurrent contact with the gas in such a manner that the liquid-gas ratio falls in the range of 2 to 15 L/Nm$^3$.

7. A method according to claim 1, wherein a retention time of the gas in the empty space of column from the upper end of a gas inlet nozzle to the tray of the lowermost level or the member for supporting the packing is in the range of 1 to 5 seconds and/or a retention time of the gas in the empty space of column from the uppermost part of a packed column to the lower end of a gas outlet nozzle is in the range of 0.5 to 3 seconds.

8. A method according to claim 1, the solvent further incorporates a polymerization inhibitor wherein the polymerization inhibitor is at least one member selected from the group consisting essentially of methoquinone, manganese acetate, nitrosophenol, cupherron, a N-oxyl compound, copper dibutylthiocarbamate, phenothiazine, and hydroquinone.

9. A method according to claim 2, the solvent further incorporates a polymerization inhibitor wherein the polymerization inhibitor is at least one member selected from the group consisting essentially of methoquinone, manganese acetate, nitrosophenol, cupherron, a N-oxyl compound, copper dibutylthiocarbamate, phenothiazine, and hydroquinone.

10. A method according to claim 2, wherein the (meth)acrylic acid and/or (meth)acrolein-containing gas is introduced into the absorption column through the lower part thereof, part of the (meth)acrylic acid and/or (meth)acrolein-containing solution withdrawn through the bottom part of the column is cooled in an external heat exchanger, and the cooling liquid is brought into countercurrent contact with the gas in such a manner that the liquid-gas ratio falls in the range of 2 to 15 L/Nm$^3$.

11. A method according to claim 1, wherein the (meth)acrylic acid and/or (meth)acrolein-containing gas is supplied to the absorption column at a temperature in the range of 100 to 300° C.

* * * * *